US008093063B2

(12) United States Patent
Albitar

(10) Patent No.: US 8,093,063 B2
(45) Date of Patent: Jan. 10, 2012

(54) ASSAY FOR DETECTING GENETIC ABNORMALITIES IN GENOMIC NUCLEIC ACIDS

(75) Inventor: Maher Albitar, Coto De Caza, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 85 days.

(21) Appl. No.: 11/947,056

(22) Filed: Nov. 29, 2007

(65) Prior Publication Data

US 2009/0142755 A1   Jun. 4, 2009

(51) Int. Cl.
*G01N 33/00* (2006.01)
*G01N 33/566* (2006.01)
*G01N 33/543* (2006.01)
*G01N 33/53* (2006.01)
*C12Q 1/68* (2006.01)
*C12M 3/00* (2006.01)
*C07H 21/04* (2006.01)

(52) U.S. Cl. ....... 436/94; 435/6.11; 435/7.1; 435/287.2; 436/501; 436/518; 536/23.1; 536/24.3

(58) Field of Classification Search .................. None
See application file for complete search history.

(56) References Cited

U.S. PATENT DOCUMENTS

| | | | |
|---|---|---|---|
| 4,737,454 A * | 4/1988 | Dattagupta et al. ........ 536/24.31 |
| 5,135,717 A | 8/1992 | Renzoni et al. |
| 5,374,524 A | 12/1994 | Miller |
| 5,539,517 A | 7/1996 | Cabib et al. |
| 5,580,990 A | 12/1996 | Van Den Berg et al. |
| 5,652,099 A | 7/1997 | Conrad |
| 5,686,247 A * | 11/1997 | Holland et al. ................... 435/6 |
| 5,714,327 A | 2/1998 | Houthoff et al. |
| 5,790,727 A | 8/1998 | Dhadwal et al. |
| 5,804,384 A | 9/1998 | Muller et al. |
| 5,846,708 A | 12/1998 | Hollis et al. |
| 5,853,984 A | 12/1998 | Davis et al. |
| 5,856,089 A | 1/1999 | Wang et al. |
| 5,880,473 A | 3/1999 | Ginestet |
| 5,922,617 A | 7/1999 | Wang et al. |
| 5,943,129 A | 8/1999 | Hoyt et al. |
| 5,985,566 A | 11/1999 | Houthoff et al. |
| 6,049,380 A | 4/2000 | Goodwin et al. |
| 6,054,279 A | 4/2000 | Nadeau et al. |
| 6,055,325 A | 4/2000 | Garini et al. |
| 6,066,459 A | 5/2000 | Garini et al. |
| 6,140,044 A | 10/2000 | Besemer et al. |
| 6,143,495 A | 11/2000 | Lizardi et al. |
| 6,191,425 B1 | 2/2001 | Imai |
| 6,235,504 B1 | 5/2001 | Zhang et al. |
| 6,252,664 B1 | 6/2001 | Barbera-Guillem |
| 6,261,776 B1 | 7/2001 | Pirrung et al. |
| 6,268,132 B1 | 7/2001 | Conrad |
| 6,277,581 B1 | 8/2001 | O'Brien et al. |
| 6,287,776 B1 | 9/2001 | Hefti |
| 6,294,331 B1 | 9/2001 | Ried et al. |
| 6,514,693 B1 | 2/2003 | Lansdorp |
| 2001/0007747 A1 | 7/2001 | Bochkariov et al. |
| 2001/0010906 A1 * | 8/2001 | Alexandre et al. ................. 435/6 |
| 2001/0018514 A1 | 8/2001 | McGall et al. |
| 2002/0119455 A1 * | 8/2002 | Chan ................................. 435/6 |
| 2003/0022204 A1 | 1/2003 | Lansdorp |
| 2003/0143585 A1 | 7/2003 | Stevens et al. |
| 2003/0194706 A1 * | 10/2003 | Brevnov ........................... 435/6 |
| 2004/0248144 A1 | 12/2004 | Mir |
| 2006/0246475 A1 | 11/2006 | Peterson et al. |
| 2006/0286570 A1 * | 12/2006 | Rowlen et al. .................... 435/6 |
| 2006/0292576 A1 | 12/2006 | Albitar et al. |
| 2007/0009954 A1 * | 1/2007 | Wang et al. ....................... 435/6 |
| 2007/0031829 A1 * | 2/2007 | Yasuno et al. .................... 435/6 |
| 2007/0042400 A1 * | 2/2007 | Choi et al. ........................ 435/6 |
| 2007/0042419 A1 * | 2/2007 | Barany et al. .................... 435/6 |

FOREIGN PATENT DOCUMENTS

| | | |
|---|---|---|
| EP | 0 237 833 | 9/1987 |
| EP | 0 539 466 | 11/1996 |
| EP | 0 742 286 | 11/1996 |
| EP | 1032701 | 9/2000 |
| WO | WO-93/18186 | 9/1993 |
| WO | WO-99/60163 | 11/1999 |
| WO | WO-00/09650 | 2/2000 |
| WO | WO-00/26412 | 5/2000 |
| WO | WO-00/42222 | 7/2000 |
| WO | WO-00/47600 | 8/2000 |
| WO | WO-00/50869 | 8/2000 |
| WO | WO-01/01144 | 1/2001 |
| WO | WO-01/46467 | 6/2001 |
| WO | WO-03/048727 | 6/2003 |

OTHER PUBLICATIONS

Zhang et al., Bioinformatics, 2003, vol. 19, No. 1, pp. 14-21.*
Zhang et al., Bioinformatics, vol. 19, No. 1, 2003, pp. 14-21.*
Baerlocher et al., Telomere length measurements in leukocyte subsets by automated multicolor flow-FISH, Cytometry Part A, 55A:1-6 (2003).
Bao et al., SNP identification in unamplified human genomic DNA with gold nanoparticle probes, Nucleic Acids Research, vol. 33. No. 2, p. 1-7, (2005).
Borucki et al., Suspension microarray with dendrimer signal amplification allows direct and high-throughput subtyping of *Listeria monocytogenes* from genomic DNA, Journal of Clinical Microbiology, vol. 43, No. 7, p. 3255-3259, (2005).
Cheung et al., Integration of cytogenetic landmarks into the draft sequence of the human genome, Nature, 409:953-958, (2001).
Fornier et al., Serum HER2 extracellular domain in metastatic breast cancer patients treated with weekly trastuzumab and paclitaxel: association with HER2 status by immunohistochemistry and fluorescence in situ hybridization and with response rate, Annals of Oncology, 16:234-239, (2005).

(Continued)

Primary Examiner — Bradley L Sisson
(74) *Attorney, Agent, or Firm* — Foley & Lardner LLP

(57) ABSTRACT

The present invention provides methods of detecting unamplifed genomic nucleic acid anchored to a solid support. The methods are useful for the detecting genetic abnormalities associated with various diseases, diagnosis, and prognosis.

48 Claims, No Drawings

OTHER PUBLICATIONS

Friedrich et al., Improved enumeration of lactic acid bacteria in mesophilic dairy starter cultures by using multiplex quantitative real-time PCR and flow cytometry-fluorescence in situ hybridization, Applied and Environmental Microbiology, vol. 72, No. 6, p. 4163-4171, (2006).

Henegariu et al., Custom fluorescent-nucleotide synthesis as an alternative method for nucleic acid labeling, Nature Biotechnology, 18:345-348, (2000).

Jameson et al., Fluorescent nucleotide analogs: Synthesis and applications, Methods in Enzymology, 278:363-390, (1997).

Keith et al., Seeding drug discovery: integrating telomerase cancer biology and cellular senescence to uncover new therapeutic opportunities in targeting cancer stem cells, Drug Discovery Today, vol. 12, No. 15/16, p. 611-621, (2007).

Kong et al., Serum HER-2 concentration in patients with primary breast cancer, Journal of Clinical Pathology, 59:373-736, (2006).

Lee et al., Age-related telomere length dynamics in peripheral blood mononuclear cells of healthy cynomolgus monkeys measured by Flow FISH, Immunology, 105:458-465, (2002).

Mansfield et al., Nucleic acid detection using non-radioactive labeling methods, Molecular and Cellular Probes, 9:145-156, (1995).

McPherson et al., A physical map of the human genome, Nature, 409:934-41, (2001).

Rao et al., Genotyping single nucleotide polymorphisms directly from genomic DNA by invasive cleavage reaction on microspheres, Nucleic Acids Research, vol. 31, No. 11, p. 1-8, (2003).

Rockenbauer et al., SNP genotyping using microsphere-linked PNA and flow cytometric detection, Cytometry Part A 64A:80-86, (2005).

Rufer et al., Telomere length dynamics in human lymphocyte subpopulations measured by flow cytometry, Nature Biotechnology, 16:743-747, (1998).

Rubin et al., The basic biology of HER2. Ann. Oncology, 12 Supp. 1:53-58, 2001.

Sambrook et al., Molecular Cloning, A Laboratory Manual, 2d, Cold Spring Harbor Laboratory Press, p. 16.54 (1989).

Sokol et al., Real time detection of DNA-RNA hybridization in living cells, Proc. Natl. Acad. Sci. USA, 95:11538-11543, (1998).

Tefferi et al., Chronic myeloid leukemia: Current application of cytogenetics and molecular testing for diagnosis and treatment, Mayo Clinic Proceedings, 80(3):390-402, (2005).

Underwood et al., C-erbB-2 gene amplification: A molecular marker in recurrent bladder tumors?, Cancer Research, 55, 2422-2430, (1995).

Van Dekkan et al., Flow cytometric quantification of human chromosome specific repetitive DNA sequence by single and bicolor fluorescent in situ hybridization to lymphocyte interphase nuclei. Cytometry, 11(1): 153-164, 1990.

Vega et al., Chromosomal translocations involved in non-Hodgkin lymphomas, Arch. Pathol. Lab. Med., 127:1148-1160, (2003).

Visakorpi et al., Sensitive detection of chromosome copy number aberrations in prostate cancer by fluorescence In Situ hybridization, American Journal of Pathology, vol. 145, No. 3, p. 624-630, (1994).

Zhang et al., Characterization of genomic breakpoints in MLL and CBP in leukemia patients with t(11;16), Genes, Chromosomes & Cancer, 41(3):257-65, (2004).

Zhang et al., E protein silencing by the leukemogenic AML1-ETO fusion protein, Science, 305:1286-9, (2004).

Zhang et al., Reproducible and inexpensive probe preparation for oligonucleotide arrays, Nucleic Acids Research, vol. 29, No. 13, p. 1-5, (2001).

Zhu et al., Directly labeled DNA probes using fluorescent nucleotides with different length linkers, Nucleic Acids Research, 22:3418-3422, (1994).

PCT Search Report dated Apr. 29, 2009 from related PCT application No. PCT/US2008/83676.

Antony et al., A Molecular Beacon Strategy for the Thermodynamic Characterization of Triplex DNA: Triplex formation at the promoter Region of Cyclin D1, Biochemistry, 40:9387-9395 (2001).

Bortolin et al: Detection of BCR-ABL Transcripts from the Philadelphia, Translocation by Hybridization in Microtiter Wells and Time-Resolved Immunofluorometry, Clinical Chemistry, vol. 41, No. 5, 1995, pp. 693-699.

Cheng et al: Array rank order regression analysis for the detection of gene copy-number changes in human cancer, Genomics, Academic Press, San Diego, US, vol. 82, No. 2,(Aug. 1, 2003), pp. 122-129.

Extended European Search Report dated Aug. 5, 2009 for EP Application No. 06773778.3.

Hamaguchi et al., Aptamer Beacons for the Direct Detection of Proteins, Anal. Biochem. 294:126-131 (2001).

International Search Report Dated May 23, 2007 for PCT Application No. PCT/US06/24321.

Ishkanian et al. A tiling resolution DNA microarry with complete coverage of the human genome. 2004. Nature Genetics. vol. 36, pp. 299-303.

Kaboev et al., PCR hot start using primers with the structure of molecular beacons (hairpin-like structure), Nucl. Acids Res. 28:E94 (2000).

Kearney et al: Rapid colorimetric assay for the detection of the bcr-abl rearrangement, Clinical and Laboratory Haematology Apr. 1998, vol. 20, No. 2, Apr. 1998), pp. 101-105.

Poddar et al, *Bordetella pertussis* detection by spectrofluorometry using polymerase chain reaction (PCR) and a molecular beacon probe, Mol. Cell. Probes 15:161-167 (2001).

Smirnov et al, Effect of Loop Sequence and Size on DNA Aptamer Stability, Biochemistry 39:1462-1468 (2000).

Yamamoto et al, Molecular beacon aptamer fluorescence in the presence of Tat protein of HIV-1, Genes Cells 5:389-396 (2000).

Extended European Search Report dated Dec. 20, 2010 in EP 08857720.

International Preliminary Report on Patentability dated Jun. 1, 2010 in related application PCT/US2008/083673.

\* cited by examiner

ASSAY FOR DETECTING GENETIC ABNORMALITIES IN GENOMIC NUCLEIC ACIDS

FIELD OF THE INVENTION

The present invention relates to the detection of genomic nucleic acid.

BACKGROUND OF THE INVENTION

The following description is provided to assist the understanding of the reader. None of the information provided or references cited is admitted to be prior art to the present invention.

Genetic abnormalities e.g. duplication, deletion, chromosomal translocation, point mutation often leads to pathological conditions.

Some diseases, such as cancer, are due to genetic abnormalities acquired in a few cells during life, while in other diseases the genetic abnormality is present in all cells of the body and present since conception.

To detect a genetic abnormality it is necessary to detect the genomic nucleic acid containing the abnormality. Methods of detection of genetic abnormalities, such as aneuploidy, translocations, duplications and deletions are well known in the art. One such methods includes cytogenetic analysis in which a metaphase spread of chromosomes is stained and visualized. Metaphase chromosomes exhibit a particular pattern of light and dark staining manifested in a chromosomal banding pattern.

The development of molecular cytogenetic approaches offer assays with greater sensitivity. These techniques incorporate DNA hybridization with radiolabeled or fluorescent labeled probes. For example, in fluorescence in situ hybridization (FISH) analysis, a fluorescent probe is hybridized to metaphase or interphase chromosomes. The hybridized probe is then detected using a fluorescence microscope. However, these methods require intact cells or intact or partially intact nuclei.

Non-in situ hybridization methods of detecting chromosomal abnormalities are also known in the art. US Patent publication 2006/0292576 describes a method of detecting chromosomal abnormalities by hybridizing, capturing, and detecting genomic DNA on a solid support. This method utilizes two probes specific for the genomic nucleic acid. One probe is anchored to the solid support and the other probe is detectably labeled. Hybridization of the first probe with the genomic nucleic acid captures the genomic nucleic acid on the solid support, while the signal from the detectable labels of the second probe is used to detect the genomic nucleic acid. This method require capturing of genomic nucleic acid to solid support by nucleic acid hybridization.

One method of detecting a single nucleotide polymorphism is by dynamic allele-specific hybridization (DASH). This method takes advantage of the differences in the melting temperature ($T_m$) in DNA that results from the instability of mismatched base pairs. The genomic segment is amplified e.g. by PCR and attached to a solid support. An allele specific oligonucleotide is added in the presence of a molecule that fluoresces when bound to double-stranded DNA. The intensity is measured as temperature is increased until the $T_m$ is determined. A mutation will result in a lower than expected Tm and thus can be distinguished from the wild type sequence.

Another method of detecting a single nucleotide polymorphism is by microarray technology. The genomic nucleic acid is initially amplified, then captured on a solid surface by hybridization to a probe anchored to the solid surface. The genomic nucleic acid is detected by hybridization using a second probe with a detectable label.

SUMMARY OF THE INVENTION

The present invention provides methods for detecting a genomic nucleic acid of interest in a test sample without amplification and without the need for intact cells or nuclei. Generally, a genomic nucleic acid is hybridized to a labeled probe and anchored to a solid support through means other than nucleic acid hybridization. The genomic nucleic acid is detected by detecting the label in the hybridized complex on the solid support. The method may be used to detect a genetic abnormality e.g., point mutation, gene duplication or deletion, and chromosomal translocation. The method may also be used for diagnosis or prognosis of a disease.

In one aspect, the invention provides a method for detecting a target sequence in genomic nucleic acid, by:
 a. contacting a sample of genomic nucleic acid containing the target sequence with a probe specific for the target sequence and forming on a solid support a complex consisting of the genomic nucleic acid and the probe hybridized to the target sequence, wherein the probe contains a detectable label, the genomic nucleic acid is anchored to the solid support through means other than nucleic acid hybridization and the target sequence of the genomic nucleic acid has not been amplified; and
 b. detecting the presence of the target sequence in the genomic nucleic acid by detecting association of the label with the solid support.

In another aspect, the invention provides a method for detecting the presence or absence of a genetic abnormality in genomic nucleic acid, by:
 a. contacting a sample of genomic nucleic acid with a probe specific for the genetic abnormality and forming on a solid support a complex consisting of the genomic nucleic acid and the probe if the genetic abnormality is present in the genomic nucleic acid, the genomic nucleic acid is anchored to the solid support through means other than nucleic acid hybridization and the target sequence of the genomic nucleic acid has not been amplified;
 b. detecting the presence of the genetic abnormality by detecting association of the label with the solid support.

In another aspect, the invention provides a method for detecting genetic abnormality in a genomic nucleic acid, by:
 a. contacting a sample of genomic nucleic acid containing the genetic abnormality with a first probe specific for the genetic abnormality and forming a first complex on a solid support consisting of the genomic nucleic acid and the first probe, wherein the probe contains a detectable label, the genomic nucleic acid is anchored to the solid support through means other than nucleic acid hybridization and the target sequence of the genomic nucleic acid has not been amplified;
 b. contacting a sample of genomic nucleic acid with a second probe specific for the reference nucleic acid and forming a second complex on a solid support consisting of the reference nucleic acid and the second probe, wherein the second probe contains a detectable label; and
 c. measuring the amount of the first complex formed by detecting the detectable label of the first probe associated with the complex and measuring the amount of second complex formed by detecting the detectable label of the second probe associated with the complex; and d. comparing the amount of the first complex to the amount of the second complex, wherein a difference in the amount of two complexes is an indicative of genetic abnormality.

In one embodiment of any of the foregoing aspects, the genomic nucleic acid and reference nucleic acid are from the same sample. In another embodiment of any of the foregoing aspects, the genomic nucleic acid and the reference nucleic acid are from a different sample, which may be from the same or different individuals. In another embodiment, the amount of first complex and the second complex are determined using the same solid support, and the detectable labels of the first probe and the second probe are different.

In another aspect, the invention provides a method for detecting genetic abnormality in a genomic nucleic acid, by:

a. contacting a sample of genomic nucleic acid containing the genetic abnormality with a first probe specific for the genetic abnormality and forming a first complex on a solid support consisting of the genomic nucleic acid and the first probe, wherein the probe contains a detectable label, the genomic nucleic acid is anchored to the solid support through means other than nucleic acid hybridization and the target sequence of the genomic nucleic acid has not been amplified;

b. contacting a sample of genomic nucleic acid with a second probe specific for the reference nucleic acid and forming a second complex on a solid support consisting of the reference nucleic acid and the second probe, wherein the second probe contains a detectable label; and c. measuring the amount of the first complex formed by detecting the detectable label of the first probe associated with the complex and measuring the amount of second complex formed by detecting the detectable label of the second probe associated with the complex; and d. obtaining a ratio of the amount of the first and the second complex; and e. comparing the ratio obtained to a ratio similarly obtained using genomic nucleic acid from a reference sample, wherein a difference in the ratios is indicative of genetic abnormality.

In preferred embodiments, the genomic nucleic acid and the reference nucleic acid are anchored to the solid support through interaction of biotin and avidin. In another preferred embodiment, the solid support is a bead. In another preferred embodiment, the first and second complexes are detected by flow cytometry.

In preferred embodiments of all aspects of this invention, the genetic abnormality is a point mutation, a chromosomal translocation, a duplication or a deletion. In one embodiment, present invention provides a method of detecting duplication of HER-2 gene.

In another aspect, the invention provides a method for diagnosis in an individual by:

a. contacting a sample of genomic nucleic acid from the individual with a probe complementary to nucleic acid sequence specific for the disease and forming on a solid support a complex consisting of the genomic nucleic acid and the probe if the genomic nucleic acid contains the nucleic acid sequence specific for the disease, wherein the probe contains a detectable label, the genomic nucleic acid is anchored to the solid support through means other than nucleic acid hybridization and the target sequence of the genomic nucleic acid has not been amplified; and b. measuring the amount of the complex formed on the solid support by detecting the amount of detectable label associated with the support; and c. comparing the amount of complex formed to the amount of complex formed using genomic nucleic acid from a reference sample assayed under similar conditions, wherein a difference in amount of complex formed from the individual as compared to the reference sample is diagnostic for the disease.

In one embodiment, the reference sample may be obtained from an individual assumed to be free of the disease. In another embodiment, the reference sample may be obtained from an individual known to have the disease. In another embodiment, the reference sample is obtained from the same individual after obtaining the first sample. In one embodiment, the method may be used for measuring tumor burden in an individual suspected of having cancer. In another embodiment, the method may be used for prognosis of a disease.

The genomic nucleic acid may be anchored covalently or non-covalently to the solid support. In some embodiments of all aspects of this invention, the genomic nucleic acid may be anchored non-covalently to the solid support via a "binding pair," which refers herein to two molecules which form a complex through a specific interaction. Thus, the genomic nucleic acid can be captured on the solid support through an interaction between one member of the binding pair linked to the genomic nucleic acid and the other member of the binding pair coupled to the solid support.

In a preferred embodiment, the binding pair is biotin and avidin, or variants of avidin e.g. streptavidin, and NeutrAvidin™.

In other embodiments, the binding pair may be a ligand-receptor, a hormone-receptor, an antigen-antibody.

In some embodiments of all aspects of this invention, the genomic nucleic acid may be anchored to the solid support through covalent linking. In one embodiment, the covalent linking of the genomic nucleic acid to the solid support is achieved through photoactive groups e.g. azido, azidophenacyl, 4-nitrophenyl 3-diazopyruvate, psolarens, psolaren derivatives. In another embodiment, the genomic nucleic acid can be cross-linked to variety of solid surfaces by UV cross linking. In another embodiment, the genomic nucleic acid may be anchored to the solid support though chemical coupling using chemical linkers.

In another preferred embodiment, the genomic nucleic acid is genomic DNA. In another embodiment, the reference nucleic acid is a house keeping gene or a single copy sequence in a chromosome.

In one embodiment of all aspects of this invention, the test sample or the reference sample containing genomic nucleic acid and reference nucleic acid, respectively, can be obtained from or accessed within cells, tissues, body fluids, plasma, serum, urine, central nervous system fluid, stool, bile duct, paraffin-embedded tissue, cell lysates, tissue lysates and the like. The test and reference nucleic acid may be obtained from any number of sources and by any method.

In one preferred embodiment of all aspects of this invention, the probe may be an oligonucleotide, artificial chromosome, fragmented artificial chromosome, genomic DNA, RNA, recombinant nucleic acid, peptide nucleic acid (PNA), hairpin oligonucleotide, or oligomer of heterocycles. In one embodiment, probes are preferably large fragments of DNA (>20 kb, including cosmid, YAC, or BAC clones).

In preferred embodiments of all aspects of this invention, the detectable label associated with the probe may be a fluorophore, a nanoparticle, an isotope, a chemiluminiscent compound, an enzyme or a hapten.

In preferred embodiments of all aspects of this invention, the detectable label can be detected by a labeled reagent. In one preferred embodiment, the labeled reagent can be a labeled antibody capable of detecting the label associated with the probe. In another embodiment, the labeled reagent is a primary antibody/secondary antibody pair capable of detecting the label associated with the probe and the primary or the secondary antibody or both are associated with a detectable label.

In some embodiments of all aspects of this invention, the complex of genomic nucleic acid anchored to a solid support, a probe having a detectable label and hybridized to the genomic nucleic acid is detected by flow cytometer.

In some embodiments of all aspects of this invention, the genomic nucleic acid is first be hybridized to a probe having a detectable label in solution and then the hybridized complex may be anchored to a solid support.

In some embodiments of all aspects of the invention, the probe may be at least 50 nucleotides in length. In other embodiments, one or more of the probes is greater than about 1,000, 1,500, 2,000, 2,500, 3,000, 4,000, 5,000, 7,500, 10,000, 20,000, 50,000, 100,000, or more nucleotides in length.

As used herein, unless otherwise stated, the singular forms "a," "an," and "the" include plural reference. Thus, for example, a reference to "an oligonucleotide" includes a plurality of oligonucleotide molecules, a reference to solid support is a reference to one or more solid supports, a reference to label is a reference to one or more labels, a reference to probe is a reference to one or more probes, and a reference to "a nucleic acid" is a reference to one or more polynucleotides.

The term "genomic nucleic acid" as used herein refers to the nucleic acid in a cell that is present in the cell chromosome(s) of an organism which contains the genes that encode the various proteins of the cells of that organism. Genomic nucleic acid also refers to the nucleic acid of a virus which provides the information for the virus. Genomic nucleic acid is usually DNA but may be RNA such as in mRNA or RNA such as in some viruses. A preferred type of genomic nucleic acid is that present in the nucleus of a eukaryotic cell. Genomic nucleic acid can be double stranded or single stranded, or partially double stranded, or partially single stranded or a hairpin molecule. Genomic nucleic acid may be intact or fragmented (e.g., digested with restriction endonucleases, or by sonication or by applying shearing force by methods known in the art). In some cases, genomic nucleic acid may include sequence from all or a portion of a single gene or from multiple genes, sequence from one or more chromosomes, or sequence from all chromosomes of a cell. As is well known, genomic nucleic acid includes gene coding regions, introns, 5' and 3' untranslated regions, 5' and 3' flanking DNA and structural segments such as telomeric and centromeric DNA, replication origins, and intergenic DNA. Genomic nucleic acid representing the total nucleic acid of the genome is referred to as "total genomic nucleic acid."

Genomic nucleic acid may be obtained by methods of extraction/purification from cells as is well known in the art. Cells from which genomic nucleic acid is obtained can be normal cells or may be cells that contain one or more mutations in the genomic nucleic acid, e.g., dupliation, deletion, translocation, and transversion. Genomic nucleic acid may directly extracted from a cell or may be a copy of nucleic acid extracted from a cell. Excluded from the meaning of genomic nucleic acid is genomic nucleic acid that has been subjected to an amplification step that increases the amount of the target sequence of interest sought to be detected relative to other nucleic acid sequences in the genomic nucleic acid.

Genomic nucleic acid can be about 10 bases, about 20 bases, about 50 bases, about 100 bases, about 500 bases, about 1,000 bases, about 2,000 bases, 2,500 bases, about 3,000 bases, about 3,500 bases, about 4,000 bases, about 5,000 bases, about 7,500 bases, about 10,000 bases, about 20,000 bases, about 30,000 bases, about 40,000 bases, about 50,000 bases, about 75,000 bases, about 100,000 bases, about 1,000,000 bases, about 2,000,000 bases, 5,000,000 bases or more.

The term "reference nucleic acid" as used herein refers to a nucleic acid which is intended to be identified for the purposes of comparison with genomic nucleic acid under investigation. Reference nucleic acid may be a DNA or RNA, natural or synthetic. In certain cases, the reference nucleic acid may contain relatively invariant sequence i.e. a housekeeping gene or locus or other gene, or other sequence in a chromosome that is not expected to change under varying conditions (e.g., a normal state or a disease state). A reference nucleic acid may also represent a nucleic acid in a normal or wild type state, that is, absent point mutations, translocations, deletions, or duplications. In another case, a reference nucleic acid may represent a nucleic acid sequence with point mutations, translocations, deletions, or duplications. In some cases, the genomic nucleic acid under investigation and the reference nucleic acid may be obtained from the same sample. In other cases, the genomic nucleic acid and the reference nucleic acid may be obtained from different samples. In some cases, reference nucleic acid may be obtained from a different source than the genomic nucleic acid. In some cases, reference nucleic acid may be obtained from a different organism than the genomic nucleic acid.

The term "target nucleic acid" and "target sequence" are used interchangeably herein and refer to nucleic acid sequence which is intended to be identified, Target sequence can be DNA or RNA. "Target sequence" may be genomic nucleic acid. Target sequences may include wild type sequences, nucleic acid sequences containing point mutations, deletions or duplications, sequence from all or a portion of a single gene or from multiple genes, sequence from one or more chromosomes, or any other sequence of interest. Target sequences may represent alternative sequences or alleles of a particular gene. Target sequence can be double stranded or single stranded, or partially double stranded, or partially single stranded or a hairpin molecule. Target sequence can be about 1-5 bases, about 10 bases, about 20 bases, about 50 bases, about 100 bases, about 500 bases, about 1,000 bases, about 2,000 bases, 2,500 bases, about 3,000 bases, about 3,000 bases, about 4,000 bases, about 5,000 bases, about 7,500 bases, about 10,000 bases, about 20,000 bases, about 30,000 bases, about 40,000 bases, about 50,000 bases, about 75,000 bases, about 100,000 bases, about 1,000,000 bases or more.

As used herein, unless indicated otherwise, "about" means plus or minus 10%.

The terms "identity" and "identical" refer to a degree of identity between sequences. There may be partial identity or complete identity. A partially identical sequence is one that is less than 100% identical to another sequence. Preferably, partially identical sequences have an overall identity of at least 70% or at least 75%, more preferably at least 80% or at least 85%, most preferably at least 90% or at least 95%.

The term "detecting" as used herein in context of detecting a signal from a detectable label to indicate the presence of a genomic nucleic acid in the sample does not require the method to provide 100% sensitivity and/or 100% specificity. As is well known, "sensitivity" is the probability that a test is positive, given that the person has a genomic nucleic acid sequence, while "specificity" is the probability that a test is negative, given that the person does not have the genomic nucleic acid sequence. A sensitivity of at least 50% is preferred, although sensitivities of at least 60%, at least 70%, at least 80%, at least 90% and at least 99% are clearly more preferred. A specificity of at least 50% is preferred, although sensitivities of at least 60%, at least 70%, at least 80%, at least 90% and at least 99% are clearly more preferred. Detecting also encompasses assays with false positives and false negatives. False negative rates may be 1%, 5%, 10%, 15%, 20% or even higher. False positive rates may be 1%, 5%, 10%, 15%, 20% or even higher.

A "fragment" in the context of a gene fragment or a chromosome fragment refers to a sequence of nucleotide residues which are at least about 10 nucleotides, at least about 20 nucleotides, at least about 25 nucleotides, at least about 30 nucleotides, at least about 40 nucleotides, at least about 50 nucleotides, at least about 100 nucleotides, at least about 250 nucleotides, at least about 500 nucleotides, at least about 1,000 nucleotides, at least about 2,000 nucleotides, at least about 5,000 nucleotides, at least about 10,000 nucleotides, at least about 20,000 nucleotides, at least about 50,000 nucleotides, at least about 100,000 nucleotides, at least about 500,000 nucleotides, at least about 1,000,000 nucleotides or more.

In certain embodiments, isolated or purified molecules may be preferred. As used herein, the terms "isolated", "purified" or "substantially purified" refer to molecules, either nucleic acid or amino acid sequences, that are removed from their natural environment, isolated or separated, and are at least 60% free, preferably 75% free, and most preferably 90% free from other components with which they are naturally associated. An isolated molecule is therefore a substantially purified molecule.

The term "test sample" as used herein refers to a sample, which contains genomic nucleic acids or be used as a source of genomic nucleic acids for the methods of the invention.

The term "reference sample" as used herein refers to a sample, which contains reference nucleic acids or be used as a source of reference nucleic acids for the methods of the invention.

The terms "solid support" and "solid surface" are used interchangeably herein and refer to beads, microparticles, microspheres, plates which are flat or consist of wells or shallow depressions or grooves, microwell surfaces, slides, glass surface, coated glass surface, surface of a reaction vessel, chromatography columns, membranes, filters, microchips, quartz, silica, paper, plastic, nitrocellulose, nylon, polypropylene, polystyrene, or other polymers, and the like, which anchor genomic nucleic acid.

The term "probe" used herein refers to objects capable of hybridizing to at least a portion of the genomic nucleic acid or reference nucleic acid. Probes may be an oligonucleotide, artificial chromosome, fragmented artificial chromosome, genomic nucleic acid, fragmented genomic nucleic acid, RNA, recombinant nucleic acid, fragmented recombinant nucleic acid, peptide nucleic acid (PNA), locked nucleic acid, oligomer of cyclic heterocycles, or conjugates of nucleic acid.

Probes can be about 10 bases, about 20 bases, about 30 bases, about 40 bases, about 50 bases, about 75 bases, about 100 bases, about 200 bases, about 300 bases, about 400 bases, about 500 bases, about 750 bases, about 1,000 bases, about 1,500 bases, about 2,000 bases, about 2,500 bases, about 3,000 bases, about 3,500 bases, about 4,000 bases, about 5,000 bases, about 7,500 bases, about 10,000 bases, about 15,000 bases, about 20,000 bases, about 25,000 bases, about 30,000 bases, about 40,000 bases, about 50,000 bases, about 75,000 bases, about 100,000 bases, about 500,000 bases, 1,000,000 bases, about 2,000,000 bases, about 5,000,000 bases or more. The longer probes, about 1,000 (1 kb) to about 5,000,000 (5 Mb) or more nucleotides in length may be derived from a chromosome or an artificial chromosomes containing nucleic acid segment of interest. In one embodiment of the invention, probes are preferably large fragments of DNA (>20 kb, including cosmid, YAC, or BAC clones).

The term "detectable label" as used herein refers to a molecule or a compound or a group of molecules or a group of compounds associated with a probe and is used to identify the probe hybridized to a genomic nucleic acid or reference nucleic acid.

In some cases, the detectable label may be detected directly. In other cases, the detectable label may be a part of a binding pair, which can then be subsequently detected. Signals from the detectable label may be detected by various means and will depend on the nature of the detectable label. Examples of means to detect detectable label include but are not limited to spectroscopic, photochemical, biochemical, immunochemical, electromagnetic, radiochemical, or chemical means, such as fluorescence, chemifluoresence, or chemiluminescence, or any other appropriate means.

The term "hybridization" as used herein, refers to the pairing of substantially complementary nucleotide sequences (strands of nucleic acid) to form a duplex or heteroduplex through formation of hydrogen bonds between complementary base pairs. It is a specific, i.e., non-random, interaction between two complementary polynucleotides. Hybridization and the strength of hybridization (i.e., the strength of the association between the nucleic acids) is influenced by such factors as the degree of complementary between the nucleic acids, stringency of the conditions involved, and the $T_m$ of the formed hybrid.

The terms "complement", "complementary" or "complementarity" as used herein with reference to polynucleotides (i.e., a sequence of nucleotides such as an oligonucleotide or a genomic nucleic acid) related by the base-pairing rules. The complement of a nucleic acid sequence as used herein refers to an oligonucleotide which, when aligned with the nucleic acid sequence such that the 5' end of one sequence is paired with the 3' end of the other, is in "antiparallel association". For example, for the sequence "5'-A-G-T-3'" is complementary to the sequence "3'-T-C-A-5'". Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

Complementarity may be "partial" in which only some of the nucleic acids' bases are matched according to the base pairing rules. Or, there may be "complete," "total," or "full" complementarity between the nucleic acids.

The term "stringency" as used herein refers to the conditions of temperature, ionic strength, and the presence of other compounds, under which nucleic acid hybridizations are conducted. With high stringency conditions, nucleic acid base pairing will occur only between nucleic acids that have a high frequency of complementary base sequences.

The term "genetic abnormality" as used herein refers to a deviation of the nucleic acid sequence from a wild-type or normal genetic sequence. A genetic abnormality may reflect a difference between the full genetic complement of an organism, or any portion thereof, as compared to a normal full genetic complement of all chromosomes in that organism. For example, a genetic abnormality may include a change in chromosomal copy number (e.g., aneuploidy), or a portion thereof (e.g., deletions, duplications, amplifications); or a change in chromosomal structure (e.g., translocations, point mutations). Genetic abnormality may be hereditary i.e., passed from generation to generation or non hereditary. Genetic abnormality may be present in some cells of an organism or in all cells of that organism.

The term "aneuploid cell" or "aneuploidy" as used herein, refers to a cell having an abnormal number of at least one chromosome in interphase.

A "test value" is obtained through a determination of the amount of complex formed on a solid support containing the genomic nucleic acid from a test sample hybridized to a detectable probe. In one embodiment, the genomic nucleic acid from test sample is suspected of having a genetic abnormality. In one embodiment, a test value also can be obtained by detecting the same chromosomal or gene sequence in a reference sample.

A "control value" is obtained through a determination of the amount of complex formed on a solid support containing the genomic nucleic acid from a reference sample hybridized to a detectable probe. In one embodiment, the target for hybridization is suspected of not having a genetic abnormality. In another embodiment, the target for hybridization is known to have a genetic abnormality. In one embodiment, the test sample and the reference sample are the same.

A "reference value" refers to a value that has been related to some other characteristic. A set of reference values can be used as a standard curve.

The test value or control value may be expressed as an "amount of" or copy number of complex. An amount of complex can be a single value or a range of values corresponding to the level of detection of incorporated label (e.g., fluorescence intensity). For example, a range of values may be used to generate a standard curve relationship between the amount of complex formed versus some other quantity (e.g., tumor burden).

The test value or control value may be expressed as a "relative amount" or "ratio" of the amount of one complex to the amount of another. In certain embodiments of the invention methods, the two complexes may be obtained using the same target gene, wherein the amount of the second complex represents a historical value or a value obtained in a parallel assay. In other embodiments, the two complexes are obtained using two different genes, the first being a gene of interest and the second being a gene not expected to change (e.g., a housekeeping gene). Relative amounts may be a single value or a range of values. For example, a range of values may be used to generate a standard curve relationship between the relative amount of complex formed versus some other quantity (e.g., tumor burden).

The terms "allele" and "allelic variant" are used interchangeably herein. An allele is any one of a number of alternative forms or sequences of the same gene occupying a given locus or position on a chromosome. A single allele for each locus is inherited separately from each parent, resulting in two alleles for each gene. An individual having two copies of the same allele of a particular gene is homozygous at that locus whereas an individual having two different alleles of a particular gene is heterozygous.

The term "diagnose" or "diagnosis" as used herein refers to the act or process of identifying or determining a disease or condition in an organism or a plant or the cause of a disease or condition by the evaluation of the signs and symptoms of the disease or disorder. Usually, a diagnosis of a disease or disorder is based on the evaluation of one or more factors and/or symptoms that are indicative of the disease. That is, a diagnosis can be made based on the presence, absence or amount of a factor which is indicative of presence or absence of the disease or condition. Each factor or symptom that is considered to be indicative for the diagnosis of a particular disease does not need be exclusively related to the particular disease; i.e. there may be differential diagnoses that can be inferred from a diagnostic factor or symptom. Likewise, there may be instances where a factor or symptom that is indicative of a particular disease is present in an individual that does not have the particular disease.

The term "prognosis" as used herein refers to a prediction of the probable course and outcome of a clinical condition or disease. A prognosis of a patient is usually made by evaluating factors or symptoms of a disease that are indicative of a favorable or unfavorable course or outcome of the disease.

The phrase "determining the prognosis" as used herein refers to the process by which the skilled artisan can predict the course or outcome of a condition in a patient. The term "prognosis" does not refer to the ability to predict the course or outcome of a condition with 100% accuracy. Instead, the skilled artisan will understand that the term "prognosis" refers to an increased probability that a certain course or outcome will occur; that is, that a course or outcome is more likely to occur in a patient exhibiting a given condition, when compared to those individuals not exhibiting the condition. A prognosis may be expressed as the amount of time a patient can be expected to survive. Alternatively, a prognosis may refer to the likelihood that the disease goes into remission or to the amount of time the disease can be expected to remain in remission. Prognosis can be expressed in various ways; for example prognosis can be expressed as a percent chance that a patient will survive after one year, five years, ten years or the like. Alternatively prognosis may be expressed as the number of years, on average, that a patient can expect to survive as a result of a condition or disease. The prognosis of a patient may be considered as an expression of relativism, with many factors affecting the ultimate outcome. For example, for patients with certain conditions, prognosis can be appropriately expressed as the likelihood that a condition may be treatable or curable, or the likelihood that a disease will go into remission, whereas for patients with more severe conditions prognosis may be more appropriately expressed as likelihood of survival for a specified period of time.

A prognosis is often determined by examining one or more prognostic factors or indicators. These are markers, such as the presence of a particular chromosomal translocation, the presence or amount of which in a patient (or a sample obtained from the patient) signal a probability that a given course or outcome will occur. The skilled artisan will understand that associating a prognostic indicator with a predisposition to an adverse outcome may involve statistical analysis.

The term "tumor burden" as used herein refers to the amount in volume or mass of tumor in an individual. This amount may be at one site, such as the primary tumor, or may be the amount in aggregate from multiple sites such as the primary and/or metastases.

DETAILED DESCRIPTION OF THE INVENTION

The present invention provides methods for detecting an unamplified genomic nucleic acid on a solid support without the need for intact cell or nucleus. The method may be used to detect a genetic abnormality in a test sample such as point mutation, translocation, deletion, and duplication. The method may also be used for diagnosis or prognosis of a disease.

Genetic Abnormality: Types, Associated Diseases

A genetic abnormality may reflect a difference between the full genetic complement or any portion thereof, of an organism, as compared to a normal full genetic complement of all chromosomes in that organism. For example, a genetic abnormality may include a change in chromosomal copy number (e.g., aneuploidy), or a portion thereof (e.g., deletions, duplications, amplifications); or a change in chromosomal structure (e.g., translocations, point mutations). A genetic abnormality may lead to pathological conditions. While some diseases, such as cancer, are due to genetic abnormalities acquired in a few cells during life, the term "genetic disease" most commonly refers to diseases present in all cells of the body and present since conception. Genetic abnormality may be hereditary or non hereditary.

Genetic duplication is any duplication of a region of the genomic sequence. It may occur as an error in homologous recombination, a retrotransposition event, or duplication of an entire chromosome. Duplication of gene has been associated with several diseases such as some cases of pagetic osteosarcoma is associated with duplication of MYC gene (*Sarcoma*, vol. 1, no. 3-4, pp. 131-134, 1997), some cases of breast cancer are associated with duplication of HER-2/neu gene (*Ann Oncol.*, 12(suppl 1):S3-S8, 2001), some cases of bladder tumor are associated with duplication of c-erb-2 gene (Cancer Res., 55, 2422-2430, 1995).

A deletion (also called gene deletion, deficiency, or deletion mutation) is a genetic aberration in which a part of a chromosome or a sequence of DNA is missing. Deletion is the loss of genetic material. Any number of nucleotides can be deleted, from a single base to an entire piece of chromosome. Deletions can be caused by errors in chromosomal crossover during meiosis. Deletions are associated with an array of genetic disorders, including some cases of male infertility and two thirds of cases of Duchenne muscular dystrophy, a deletion of part of the short arm of chromosome 5 results in a syndrome called Cri du chat, also known as "cry of the cat" syndrome.

A chromosome "translocation" is the interchange of parts between nonhomologous chromosomes. It is generally detected through cytogenetics or a karyotyping of affected cells. There are two main types, reciprocal, in which all of the chromosomal material is retained and Robertsonian, in which some of the chromosomal material is lost. Further, translocations can be balanced (in an even exchange of material with no genetic information extra or missing) or unbalanced (where the exchange of chromosome material is unequal resulting in extra or missing genes).

A reciprocal translocation between chromosomes 9 and 22 resulting in a cytogenetically distinct acrocentric chromosome termed the Philadelphia chromosome. This translocation fuses the BCR gene locus of chromosome 22 and the proto-oncogene ABL locus of chromosome 9 to form a bcr/abl oncogenic protein (Tefferi et al. Mayo Clin Proc 80(3): 390-402, 2005). Although the Philadelphia chromosome was first associated with CML, it is now known to be an indicator of prognosis in other blood disorders such as acute lymphoblastic leukemia (ALL).

Translocations have been linked with other diseases. For example, the fusion of the CBP gene of chromosome 16 to the MLL gene of chromosome 11 through a translocation between chromosomes 11 and 16 has been associated with leukemia (Zhang et al. Genes Chromosomes Cancer 41(3): 257-65, 2004). Similarly, a translocation between chromosomes 8 and 21, resulting in a fusion of the AML1 and ETO genes is involved in nearly 15% of acute myeloid leukemia (AML) cases (Zhang et al. Science 305:1286-9, 2004). Further, a number of chromosomal translocations have been identified in various forms of lymphoma. For example, a translocation between chromosomes 8 and 14 involving the c-myc gene is reported to be present in approximately 80-85% of Burkitt lymphoma/leukemia cases (Vega et al. Arch Pathol Lab Med 127:1148-1160, 2003).

Mutations may be point mutations insertions, or deletions. A point mutation, or substitution, is a type of mutation that causes the replacement of a single base nucleotide with another nucleotide. Insertion and deletion includes insertions or deletions of a single base pair. Mutations in the gene or chromosome often is associated with diseases such as sickle cell anemia, cystic fibrosis, hemophilia, phenylketonuria, spina bifida etc.

Diagnosis of genetic abnormalities involves identification of the genomic nucleic acid sequence containing the variation in sequence from the wild-type sequence. In preferred embodiments, test samples containing the genomic nucleic acid are collected and the presence of genomic nucleic acid are identified, wherein the presence or absence of genomic nucleic acid is diagnostic.

Biological Sample Collection and Preparation

Test Sample and Reference Sample: Test sample and reference sample contains genomic nucleic acid and reference nucleic acid respectively. The test sample and reference sample may be of human or non-human origin. Test sample and reference sample may be obtained from eukaryotic or prokaryotic organisms, or plants, or environment. The test sample and reference sample may be solid, liquid, semisolid, gas, with or without any cell or tissue. Test samples and reference sample may include, but are not limited to, amniotic fluid, biopsies, blood, blood cells, bone marrow, cerebrospinal fluid, fecal samples, excrements, fine needle biopsy samples, peritoneal fluid, plasma, pleural fluid, bronchial alveolar lavage, bronchial wash, saliva, semen, serum, sputum, tears, buccal swab, tissue, tissue homogenates, frozen tissue, paraffin sections of tissue, tissue culture media, cells, cell lysates, cell from culture, cell culture supernatant, fetus, embryo, urine, microbes, virus, mycoplasma.

In one embodiment, the test sample may be obtained from an individual who is suspected of having a disease, or a genetic abnormality. In another embodiment test sample may be obtained from a healthy individual who is assumed of having no disease, or a genetic abnormality.

Sample Collection: Methods of obtaining test samples and reference samples are well known to those of skill in the art and include, but are not limited to, aspirations, tissue sections, drawing of blood or other fluids, surgical or needle biopsies, collection of paraffin embedded tissue, collection of body fluids, collection of stool, and the like.

The inventive methods can be used to perform prenatal diagnosis using any type of embryonic or fetal cell or nucleic acid containing body fluid. Fetal cells can be obtained through the pregnant female, or from a sample of an embryo. Thus, fetal cells are present in amniotic fluid obtained by amniocentesis, chorionic villi aspirated by syringe, percutaneous umbilical blood, a fetal skin biopsy, a blastomere from a four-cell to eight-cell stage embryo (pre-implantation), or a trophectoderm sample from a blastocyst (pre-implantation or by uterine lavage).

Genomic nucleic acid: In one embodiment, genomic nucleic acid may be intact. In another embodiment, genomic nucleic acid may be fragmented (e.g., digested with restriction endonucleases, or by sonication or by applying shearing force by methods known in the art).

Sample Preparation: The nucleic acid (DNA or RNA) may be isolated from the sample according to any methods well known to those of skill in the art. If necessary, the sample may be collected or concentrated by centrifugation and the like. The sample may be subjected to lysis, such as by treatments with enzymes, heat, surfactants, ultrasonication, or a combination thereof. The lysis treatment is performed in order to obtain a sufficient amount of nucleic acid. The sample may be subjected to liquid chromatography to partially purify the genomic nucleic acid.

Suitable DNA isolation methods include phenol and chloroform extraction. See Maniatis et al., Molecular Cloning, A Laboratory Manual, 2d, Cold Spring Harbor Laboratory Press, page 16.54 (1989). Numerous commercial kits also yield suitable DNA including, but not limited to, QIAamp™ mini blood kit, Agencourt Genfind™, Roche Cobas® Roche MagNA Pure® or phenol:chloroform extraction using Eppendorf Phase Lock Gels®.

Total DNA (e.g., genomic, mitochondrial, microbial, viral,) can be purified from any biological sample such as whole blood, plasma, serum, buffy coat, bone marrow, other body fluids, lymphocytes, cultured cells, tissue, and forensic specimens using commercially available kits e.g. QIAamp DNA and QIAamp DNA Blood mini kits from Qiagen. Viral RNA can be purified from whole blood, plasma, serum, buffy coat, bone marrow, other body fluids, lymphocytes, cultured cells, tissue, and forensic specimens using commercially available kits e.g. QIAamp Viral RNA mini kit.

Genomic DNA may be isolated from cells or tissues using standard methods, see, e.g., Sambrook, et al., 1989, Molecular Cloning: A Laboratory Manual, Second Edition, Cold Spring Harbor Press, Plainview, N.Y.

In another embodiment, genomic nucleic acid may be mRNA or cDNA generated from mRNA or total RNA may be used. RNA is isolated from cells or tissue samples using standard techniques, see, e.g., Sambrook, et al., 1989, Molecular Cloning: A Laboratory Manual, Second Edition, Cold Spring Harbor Press, Plainview, N.Y. In addition kits for isolating mRNA and synthesizing cDNA are commercially available e.g. RNeasy Protect Mini kit, RNeasy Protect Cell Mini kit from Qiagen.

In one embodiment, the genomic nucleic acid is DNA isolated from paraffin embedded tissue. Methods of extracting DNA from paraffin embedded tissue is well known in the art e.g. paraffin blocks containing the tissue are collected, de-waxed by treatment with xylene, treated with proteinase to remove protein contaminants, and then finally extracted with phenol and chloroform, followed by ethanol precipitation. Alternatively, DNA from a paraffin embedded tissue can be isolated by commercially available kits e.g. DNA can be isolated from paraffin embedded tissue using EZ1 DNA kit, QIAamp DNA Mini Kit from Qiagen.

Nucleic acid need not be extracted, but may be made available by suitable treatment of cells or tissue such as described in U.S. patent application Ser. No. 11/566169.

Solid Supports

Solid supports may be used to anchor genomic nucleic acid by covalent or non-covalent means. In preferred embodiments, the solid surface is a bead. In some embodiments, beads or microparticles are substantially the same size. In other embodiments, beads or microparticles are of one or more sizes. In one embodiment, the beads or microparticles may be magnetic. These beads or microparticles may be composed of, for example, polystyrene or latex. Beads or microparticles may be approximately 0.1 µm-10 µm in diameter or may be as large as 50 µm-100 µm in diameter, however, smaller and larger bead sizes are possible.

In preferred embodiments, the solid surface is a streptavidin coated bead. Streptavidin coated beads are available commercially e.g. from Bang laboratories (Catalog No. 214, 217), EMD Biosciences (Catalog No. 70716-3, 70716-4), Dynal beads from Invitrogen Corporation (Catalog No. 658-01D, 602-10).

In some embodiments, the solid surfaces may have functional groups capable of covalently linking genomic nucleic acid directly or indirectly through chemical linkers. Examples of functional groups include but not limited to poly L-lysine, aminosilane, epoxysilane, aldehydes, amino groups, epoxy groups, cyano groups, ethylenic groups, hydroxyl groups, thiol groups.

Anchoring of Nucleic Acid on Solid Support

Anchoring of the genomic nucleic acid or reference nucleic acid to the solid support may be done prior to, subsequent to, or simultaneously with hybridization of the genomic nucleic acids or reference nucleic acid to the probe having a detectable label. Nucleic acids may be anchored covalently or non-covalently to the support.

A preferred method of non-covalently anchoring nucleic acids to the solid surface is via a "binding pair," which refers herein to two molecules which form a complex through a specific interaction. Thus, the nucleic acids can be captured on the solid support through an interaction between one member of the binding pair linked to the nucleic acids and the other member of the binding pair coupled to the solid support.

In a preferred embodiment, the binding pair is biotin and avidin, or variants of avidin such as streptavidin, NeutrAvidin™. The solid surface comprises streptavidin or its variants and the genomic nucleic acid is modified to consist of biotin. Methods for biotinylating nucleic acid are known in the art (e.g. by photo-cross linking using EZ-link psoralen-PEO biotin from Pierce Chemical Co., by chemical coupling using Label IT® µArray® Biotin Labeling Kit from Mirus Bio Corp., PFP Biotin from Pierce Chemical Co., by nick translation using BioNick DNA Labeling System from Invitrogen corporation, or by 3'-end labeling using commercially available kits e.g. Biotin 3-end labeling kit from Pierce).

In other embodiments, the binding pair consists of a ligand-receptor, a hormone-receptor, an antigen-antibody. Examples of such binding pair include but are not limited to digoxigenin and anti-digoxigenin antibody; 6-(2,4-dinitrophenyl)amino-hexanoic acid and anti-dinitrophenyl antibody; 5-Bromo-dUTP (BrdUTP) and anti-BrdUTP antibody; N-acetyl 2-aminofluorene (AAF) and anti-AAF antibody. The solid surface in these cases consist of the antibody, and the genomic nucleic acid is modified to consists of the antigen. Methods of incorporating digoxigenin, 2,4-dinitrophenyl group, 5-Bromo-dUTP group into DNA can be achieved by nick translation, or by terminal transferase reaction, examples of which are amply documented in the art or may be achieved by using commercially available kits e.g. kits DIG DNA labeling kit from Roche Applied Sciences. Digoxigenin can be chemically coupled to the nucleic acid with Digoxigenin-NHS-ester. N-acetyl 2-aminofluorene (AAF) can be covalently coupled to the genomic nucleic acid.

In another embodiment, the genomic nucleic acid may be anchored to the solid support covalently though chemical coupling using chemical linkers. If covalent bonding between the genomic nucleic acid and the surface is desired, the solid surface will usually be functional or be capable of being functionalized. Examples of functional groups used for linking include but are not limited to carboxylic acids, aldehydes, amino groups, cyano groups, ethylenic groups, hydroxyl groups, thiol groups.

In some embodiments, the solid support may be coated with epoxy group, amino group, mercapto group, polylysine. Coated solid supports are available commercially e.g. beads coated with functional groups are available from Invitrogen Corporation, BD Biosciences; glass slides coated with functional groups are available from Pierce, Asper Biotech, Full Moon Biosystems, ThermoFisher Inc.

The genomic nucleic acid may be modified to consist of functional groups. The 5' phosphate group of genomic nucleic acid, may be conjugated to primary amine-containing molecules using the carbodiimide crosslinker EDC (Pierce Product No. 22980) and imidazole. The 5' phosphate group of a nucleic acid may be modified to consist of amine group with an excess of ethylenediamine, and using carbodiimide crosslinker EDC (Pierce Product No. 22980) and imidazole as described in Pierce Technote No. 30. Depending on the amine containing molecules used, the crosslinking strategy can be adapted in a number of ways to directly or indirectly modify, label or conjugate genomic nucleic acid. For example, to create a photoactivable (random-reactive) nucleic acid, p-azidobenzoyl hydrazide, (ABH, Pierce catalog No. 21510) may be used instead of ethylenediamine in the default reaction. To create a sulfhydryl-reactive nucleic acid, [N-e-Maleimidocaproic acid]hydrazide, trifluoroacetic acid salt (EMCH, Pierce catalog No. 22106), N-[k-Maleimidoundecanoic acid]hydrazide, (KMUH Pierce catalog No. 22111), or 4-(4-N-Maleimidophenyl)butyric acid hydrazide hydrochloride, (MPBH Pierce catalog No. 22305) may be used instead of ethylenediame in the default reaction. To obtain a sulfhydryl crosslink that is reversible 3-(2-Pyridyldithio)propionyl hydrazide (PDPH, Pierce catalog No. 22301) may be used instead of ethylenediamine. This strategy is useful for linking genomic nucleic acid to sulfhydryl-containing solid support. To create a sulfhydryl group on genomic nucleic acid cystamine ($NH_2$—$CH_2$—$CH_2$—S—S—$CH_2$—$CH_2$—$NH_2$) may be used instead of ethylenediamine in the default reaction, and then reduce the disulfide bond with DTT or similar reagent. This strategy is useful for covalently coupling to maleimide activated solid support. To immobilize nucleic acid to a beaded affinity support, UltraLink Hydrazide (Pierce catalog No. 53149) may be used instead of ethylenediamine in the default reaction.

The genomic nucleic acid may be modified enzymatically to consist of functional groups such as amino group e.g. incorporating amino allyl dUTP by nick translation or by terminal transferase reaction.

The manner of linking a wide variety of functional groups to each other is well known and is amply illustrated in the literature. In one embodiment, the chemical linkers may be used to covalently link two functional groups, one on the solid support and the other on the genomic nucleic acid. The chemical linkers may be mono functional, bifunctional, polyfunctional, hetero-bifunctional, or hetero-polyfunctional. In preferred embodiments, the chemical linkers may have spacer arms to avoid steric hindrance. Examples of chemical linkers to couple amino group to an amino group include but are not limited to ethylene glycol bis[succinimidylsuccinate], disuccinimidyl suberate, 1,5-difluoro-2,4-dinitrobenzene. Examples of chemical linkers to couple thiol group to a thiol group include but are not limited to 1,4-di-[3'-(2'-pyridyldithio)-propionamido]butane, dithio-bismaleimidoethane. A wide variety of suitable cross linkers and the methods of cross linking are available from Pierce.

In another embodiment, the genomic nucleic acid is anchored to the solid support through photoactive moieties. In one embodiment, the solid surface may anchor photoactive moieties capable of coupling the genomic nucleic acid by photo activation. In another embodiment, the 5' phosphate group of genomic nucleic acid, may be conjugated to a photoactive group, capable of photocrosslinking to functional groups on the solid surface. In another embodiment, the genomic nucleic acid may be anchored to the solid surface through a linker having two or more photoactive moieties, one or more at each end, wherein the linker couples to the solid surface and to the genomic nucleic acid upon exposing the solid surface and genomic nucleic acid in presence of the linker with radiation of suitable wavelength. Examples of photoactive moieties include but not limited to azides, aryl azides, azidophenacyl, 4-nitrophenyl 3-diazopyruvate, psolarens, psolaren derivatives.

In another embodiment, the genomic nucleic acid can be cross-linked to nylon, nitrocellulose, or nylon-reinforced nitrocellulose membranes, coated glass surface by exposing the solid surface and the genomic nucleic acid to ultra-violet radiation. The manner of cross-linking linking of nucleic acid to various surfaces is well known and is amply illustrated in the literature (e.g. using Stratagene UV crosslinker).

Probes

Probes are capable of hybridizing to at least a portion of the genomic nucleic acid. In a preferred embodiment, the nucleic acid probes are derived from one, several or all of the human genomic nucleic acid segments provided in a compendium of bacterial artificial chromosomes (BACs) compiled by The BAC Resource Consortium. These probes are usually referred to in the art by their RPI or CTB clone names, see Cheung et al, *Nature* 409:953-958, 2001. This compendium contains 7,600 cytogenetically defined landmarks on the draft sequence of the human genome (see McPherson et al, *Nature* 409:934-41, 2001). These landmarks are large-insert clones mapped to chromosome bands by fluorescence in situ hybridization, each containing a sequence tag that is positioned on the genomic sequence. These clones represent all 24 human chromosomes in about 1 Mb resolution. Sources of BAC genomic collections include the BACPAC Resources Center (CHORI—Children's Hospital Oakland Research Institute), ResGen (Research Genetics through Invitrogen) and The Sanger Center (UK).

Probes consist of a detectable label or a plurality of detectable labels. In one preferred embodiment, the detectable label associated with the probe can generate a detectable signal directly. In another embodiment, the detectable label associated with the probe can be detected indirectly using a reagent, wherein the reagent includes a detectable label, and binds to the label associated with the probe. In one embodiment the reagent includes a detectable label is a labeled antibody. In another embodiment the reagent including a detectable label is a primary antibody/secondary antibody pair, wherein the detectable label may be in the primary antibody, or in the secondary antibody or in both.

Hybridization

The degree of complementarity between nucleic acid strands has significant effects on the efficiency and strength of hybridization between nucleic acid strands. This is of particular importance in detection methods that depend upon binding between nucleic acids. In one embodiment, the complementarity between the probe and the genomic nucleic acid may be "partial" in which only some of the nucleic acids' bases are matched according to the base pairing rules. In another embodiment, complementarity between the probe and the genomic nucleic acid may be "complete," "total," or "full".

The methods of the present invention can incorporate all known methods and means and variations thereof for carrying out DNA hybridization, see, e.g., Sambrook, et al., 1989, Molecular Cloning: A Laboratory Manual, Second Edition, Cold Spring Harbor Press, Plainview, N.Y.

The genomic nucleic acid and reference nucleic acids and probes chosen for the nucleic acids are contacted under hybridization conditions. Hybridization conditions for nucleic acids in the methods of the present invention are well known in the art. For example, hybridization conditions may be high, moderate or low stringency conditions. Ideally, nucleic acids will hybridize only to complementary nucleic acids and will not hybridize to other non-complementary nucleic acids in the sample. The hybridization conditions can be varied to alter the degree of stringency in the hybridization and reduce background signals as is known in the art. For example, if the hybridization conditions are high stringency conditions, a nucleic acid will detectably bind to nucleic acid target sequences with a very high degree of complementarity. Low stringency hybridization conditions will allow for hybridization of sequences with some degree of sequence divergence. The hybridization conditions will vary depending on the biological sample, and the type and sequence of nucleic acids. One skilled in the art will know how to optimize the hybridization conditions to practice the methods of the present invention.

Exemplary hybridization conditions are as follows. High stringency generally refers to conditions that permit hybridization of only those nucleic acid sequences that form stable hybrids in 0.018M NaCl at 65° C. High stringency conditions can be provided, for example, by hybridization in 50% formamide, 5× Denhardt's solution, 5×SSC (saline sodium citrate) 0.2% SDS (sodium dodecyl sulphate) at 42° C., followed by washing in 0.1×SSC, and 0.1% SDS at 65° C. Moderate stringency refers to conditions equivalent to hybridization in 50% formamide, 5× Denhardt's solution, 5×SSC, 0.2% SDS at 42° C., followed by washing in 0.2× SSC, 0.2% SDS, at 65° C. Low stringency refers to conditions equivalent to hybridization in 10% formamide, 5× Denhardt's solution, 6×SSC, 0.2% SDS, followed by washing in 1×SSC, 0.2% SDS, at 50° C.

Detectable Label

The term "detectable label" as used herein refers to a molecule or a compound or a group of molecules or a group of compounds associated with a probe and is used to identify the probe hybridized to a genomic nucleic acid or reference nucleic acid.

Detectable labels include but are not limited to fluorophores, isotopes (e.g. $^{32}P$, $^{33}P$, $^{35}S$, $^{3}H$, $^{14}C$, $^{125}I$, $^{131}I$), electron-dense reagents (e.g., gold, silver), nanoparticles, enzymes commonly used in an ELISA (e.g., horseradish peroxidase, beta-galactosidase, luciferase, alkaline phosphatase), chemiluminiscent compound, calorimetric labels (e.g., colloidal gold), magnetic labels (e.g., Dynabeads™), biotin, digoxigenin, haptens, proteins for which antisera or monoclonal antibodies are available, ligands, hormones, oligonucleotides capable of forming a complex with the corresponding oligonucleotide complement.

In a preferred embodiment, the detectable label is a fluorophore. The term "fluorophore" as used herein refers to a molecule that absorbs light at a particular wavelength (excitation frequency), and subsequently emits light of a different, typically longer, wavelength (emission frequency) in response. In one embodiment, the detectable label is a donor fluorophore in close proximity of a quencher moiety.

Suitable fluorescent moieties include but are not limited to the following fluorophores working individually or in combination:
4-acetamido-4'-isothiocyanatostilbene-2,2'disulfonic acid; acridine and derivatives: acridine, acridine isothiocyanate; Alexa Fluors: Alexa Fluor® 350, Alexa Fluor® 488, Alexa Fluor® 546, Alexa Fluor® 555, Alexa Fluor® 568, Alexa Fluor® 594, Alexa Fluor® 647 (Molecular Probes); 5-(2'-aminoethyl)aminonaphthalene-1-sulfonic acid (EDANS); 4-amino-N-[3-vinylsulfonyl)phenyl]naphthalimide-3,5 disulfonate (Lucifer Yellow VS); N-(4-anilino-1-naphthyl)maleimide; anthranilamide; Black Hole Quencher™ (BHQ™) dyes (biosearch Technologies); BODIPY dyes: BODIPY® R-6G, BOPIPY® 530/550, BODIPY® FL; Brilliant Yellow; coumarin and derivatives: coumarin, 7-amino-4-methylcoumarin (AMC, Coumarin 120), 7-amino-4-trifluoromethylcouluarin (Coumarin 151); Cy2®, Cy3®, Cy3.5®, Cy5®, Cy5.5®; cyanosine; 4',6-diaminidino-2-phenylindole (DAPI); 5',5''-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); Eclipse™ (Epoch Biosciences Inc.); eosin and derivatives: eosin, eosin isothiocyanate; erythrosin and derivatives: erythrosin B, erythrosin isothiocyanate; ethidium; fluorescein and derivatives: 5-carboxyfluorescein (FAM), 5-(4,6-dichlorotriazin-2-yl)aminofluorescein (DTAF), 2',7'-dimethoxy-4'5'-dichloro-6-carboxyfluorescein (JOE), fluorescein, fluorescein isothiocyanate (FITC), hexachloro-6-carboxyfluorescein (HEX), QFITC (XRITC), tetrachlorofluorescein (TET); fluorescamine; IR144; IR1446; lanthamide phosphors; Malachite Green isothiocyanate; 4-methylumbelliferone; ortho cresolphthalein; nitrotyrosine; pararosaniline; Phenol Red; B-phycoerythrin, R-phycoerythrin; allophycocyanin; o-phthaldialdehyde; Oregon Green®; propidium iodide; pyrene and derivatives: pyrene, pyrene butyrate, succinimidyl 1-pyrene butyrate; QSY®7; QSY®9; QSY®21; QSY®35 (Molecular Probes); Reactive Red 4 (Cibacron® Brilliant Red 3B-A); rhodamine and derivatives: 6-carboxy-X-rhodamine (ROX), 6-carboxyrhodamine (R6G), lissamine rhodamine B sulfonyl chloride, rhodamine (Rhod), rhodamine B, rhodamine 123, rhodamine green, rhodamine X isothiocyanate, riboflavin, rosolic acid, sulforhodamine B, sulforhodamine 101, sulfonyl chloride derivative of sulforhodamine 101 (Texas Red); terbium chelate derivatives; N,N,N',N'-tetramethyl-6-carboxyrhodamine (TAMRA); tetramethyl rhodamine; tetramethyl rhodamine isothiocyanate (TRITC).

Other fluorescent nucleotide analogs can be used, see, e.g., Jameson, Meth. Enzymol. 278:363-390, 1997; Zhu, Nucl. Acids Res. 22:3418-3422, 1994. U.S. Pat. Nos. 5,652,099 and 6,268,132 also describe nucleoside analogs for incorporation into nucleic acids, e.g., DNA and/or RNA, or oligonucleotides, via either enzymatic or chemical synthesis to produce fluorescent oligonucleotides. U.S. Pat. No. 5,135,717 describes phthalocyanine and tetrabenztriazaporphyrin reagents for use as fluorescent labels.

The detectable label can be incorporated into, associated with or conjugated to a nucleic acid. Label can be attached by spacer arms of various lengths to reduce potential steric hindrance or impact on other useful or desired properties. See, e.g., Mansfield, *Mol. Cell. Probes* 9:145-156, 1995.

Detectable labels can be incorporated into nucleic acid probes by covalent or non-covalent means, e.g., by transcription, such as by random-primer labeling using Klenow polymerase, or nick translation, or, amplification, or equivalent as is known in the art. For example, a nucleotide base is conjugated to a detectable moiety, such as a fluorescent dye, e.g., $Cy_3$™ or Cy5,™ and then incorporated into nucleic acid probes during nucleic acid synthesis or amplification. Nucleic acid probes can thereby be labeled when synthesized using Cy3™- or Cy5™-dCTP conjugates mixed with unlabeled dCTP.

Nucleic acid probes can be labeled by using PCR or nick translation in the presence of labeled precursor nucleotides, for example, modified nucleotides synthesized by coupling allylamine-dUTP to the succinimidyl-ester derivatives of the fluorescent dyes or haptens (such as biotin or digoxigenin) can be used; this method allows custom preparation of most common fluorescent nucleotides, see, e.g., Henegariu, *Nat. Biotechnol.* 18:345-348, 2000.

Nucleic acid probes may be labeled by non-covalent means known in the art. For example, Kreatech Biotechnology's Universal Linkage System® (ULS®) provides a non-enzymatic labeling technology, wherein a platinum group forms a co-ordinative bond with DNA, RNA or nucleotides by binding to the N7 position of guanosine. This technology may also be used to label proteins by binding to nitrogen and sulfur containing side chains of amino acids. See, e.g., U.S. Pat. Nos. 5,580,990; 5,714,327; and 5,985,566; and European Patent No. 0539466.

Labeling with a detectable label also can include a nucleic acid attached to another biological molecule, such as a nucleic acid, e.g., an oligonucleotide, or a nucleic acid in the form of a stem-loop structure as a "molecular beacon" or an "aptamer beacon". Molecular beacons as detectable moieties are well known in the art; for example, Sokol (*Proc. Natl. Acad. Sci. USA* 95:11538-11543, 1998) synthesized "molecular beacon" reporter oligodeoxynucleotides with matched fluorescent donor and acceptor chromophores on their 5' and 3' ends. In the absence of a complementary nucleic acid strand, the molecular beacon remains in a stem-loop conformation where fluorescence resonance energy transfer prevents signal emission. On hybridization with a complementary sequence, the stem-loop structure opens increasing the physical distance between the donor and acceptor moieties thereby reducing fluorescence resonance energy transfer and allowing a detectable signal to be emitted when the beacon is excited by light of the appropriate wavelength. See also, e.g., Antony (*Biochemistry* 40:9387-9395, 2001), describing a molecular beacon consist of a G-rich 18-mer triplex forming oligodeoxyribonucleotide. See also U.S. Pat. Nos. 6,277,581 and 6,235,504.

Aptamer beacons are similar to molecular beacons; see, e.g., Hamaguchi, *Anal. Biochem.* 294:126-131, 2001; Poddar, *Mol Cell. Probes* 15:161-167, 2001; Kaboev, *Nucl. Acids Res.* 28:E94, 2000. Aptamer beacons can adopt two or more conformations, one of which allows ligand binding. A fluorescence-quenching pair is used to report changes in conformation induced by ligand binding. See also, e.g., Yamamoto, *Genes Cells* 5:389-396, 2000; Smimov, *Biochemistry* 39:1462-1468, 2000.

The nucleic acid probe may be indirectly detectably labeled via a peptide. A peptide can be made detectable by incorporating predetermined polypeptide epitopes recognized by a secondary reporter (e.g., leucine zipper pair sequences, binding sites for secondary antibodies, transcriptional activator polypeptide, metal binding domains, epitope tags). A label may also be attached via a second peptide that interacts with the first peptide (e.g., S—S association).

As readily recognized by one of skill in the art, detection of the complex containing the genomic nucleic acid hybridized to a labeled probe can be achieved through use of a labeled antibody against the label of the probe. In a preferred embodiment, the probe is labeled with digoxigenin and is detected with a fluorescent labeled anti-digoxigenin antibody. In another embodiment, the probe is labeled with FITC, and detected with fluorescent labeled anti-FITC antibody. These antibodies are readily available commercially. In another embodiment, the probe is labeled with FITC, and detected with anti-FITC antibody primary antibody and a labeled anti-anti FITC secondary antibody.

Detection of Genomic Nucleic Acid and Probe Complex

Methods of detection of detectably labeled probes incorporated into the hybridized genomic nucleic acid, probe and solid support complex are known in the art and vary dependent with the nature of the label.

Fluorescent dyes are detected through exposure of the label to a photon of energy of one wavelength, supplied by an external source such as an incandescent lamp or laser, causing the fluorophore to be transformed into an excited state. The fluorophore then emits the absorbed energy in a longer wavelength than the excitation wavelength which can be measured as fluorescence by standard instruments containing fluorescence detectors. Exemplary fluorescence instruments include spectrofluorometers and microplate readers, fluorescence microscopes, fluorescence scanners, and flow cytometers.

Devices and methods for the detection of multiple fluorophores are well known in the art, see, e.g., U.S. Pat. Nos. 5,539,517; 6,049,380; 6,054,279; 6,055,325; and 6,294,331. Any known device or method, or variation thereof, can be used or adapted to practice the methods of the invention, including array reading or "scanning" devices, such as scanning and analyzing multicolor fluorescence images; see, e.g., U.S. Pat. Nos. 6,294,331; 6,261,776; 6,252,664; 6,191,425; 6,143,495; 6,140,044; 6,066,459; 5,943,129; 5,922,617; 5,880,473; 5,846,708; 5,790,727; and, the patents cited in the discussion of arrays, herein. See also published U.S. Patent Application Nos. 2001/0018514; 2001/0007747; and published international patent applications Nos. WO/0146467A; WO/9960163A; WO/0009650A; WO/0026412A; WO/0042222A; WO/0047600A; and WO/0101144A.

Charge-coupled devices, or CCDs, are used in microarray scanning systems, including practicing the methods of the invention. Color discrimination can also be based on 3-color CCD video images; these can be performed by measuring hue values. Hue values are introduced to specify colors numerically. Calculation is based on intensities of red, green and blue light (RGB) as recorded by the separate channels of the camera. The formulation used for transforming the RGB values into hue, however, simplifies the data and does not make reference to the true physical properties of light. Alternatively, spectral imaging can be used; it analyzes light as the intensity per wavelength, which is the only quantity by which to describe the color of light correctly. In addition, spectral imaging can provide spatial data, because it contains spectral information for every pixel in the image. Alternatively, a spectral image can be made using brightfield microscopy, see, e.g., U.S. Pat. No. 6,294,331.

In a preferred embodiment, hybridized complexes are detected using flow cytometry. Flow cytometry is a technique well-known in the art. Flow cytometers hydrodynamically focus a liquid suspension of particles (e.g., cells or synthetic microparticles or beads) into an essentially single-file stream of particles such that each particle can be analyzed individually. Flow cytometers are capable of measuring forward and side light scattering which correlates with the size of the particle. Thus, particles of differing sizes may be used in invention methods simultaneously to detect distinct nucleic acid segments. In addition fluorescence at one or more wavelengths can be measured simultaneously. Consequently, particles can be sorted by size and the fluorescence of one or more fluorescent labels probes can be analyzed for each particle. Exemplary flow cytometers include the Becton-Dickenson Immunocytometry Systems FACSCAN. Equivalent flow cytometers can also be used in the invention methods.

In another embodiment, the complex containing genomic nucleic acid anchored to the solid support and hybridized to the probe may be detected by surface Plasmon resonance.

In some embodiments in all aspects of this invention, the method is suitable for large abnormalities such as involving at least 50 bases, more preferably at least 100 bases, more preferably at least 200 bases, more preferably at least 500 bases, more preferably at least 1 kb, more preferably at least 2 kb, more preferably at least 4 kb, more preferably at least 8 kb, and even more preferably at least 10 kb or more. However, smaller abnormalities may be detected including at least one base, at least 5 bases, at least 10 bases, at least 25 bases, at least 25-50 bases by appropriate adjustment of probes and hybridization conditions as is well known in the art.

A method for detecting a duplication or deletion of a chromosomal segment or gene is shown in examples 1-4. The sequence of interest in these particular examples is human HER-2 gene. Amplification of HER-2 gene has been documented to be associated with breast cancer. Genomic DNA is isolated from serum of individuals documented to have breast cancer for test cases. For control cases, genomic DNA is isolated from individuals documented not to have breast cancer. The genomic DNA is biotinylated and hybridized to two probes. One of the probe is complimentary to a region of the HER-2 gene and labeled with FITC. The other probe is complimentary to a region of chromosome 17 specific single copy sequence (17-SSC) and labeled with Cy5. The biotinylated genomic DNA hybridized to the two probes is then anchored to streptavidin coated beads available commercially. The signal from HER-2 probe is further enhanced by binding the complex to rabbit anti-FITC/goat anti rabbit Alexa-488 antibodies. Flow cytometry is used to detect the hybridization complex captured on the beads. Ratio of the signal obtained from the HER-2 probe/Antibody pair and from 17-SSC are measured. The ratio of the signal from test cases are compared to control cases. A greater ratio is considered an amplification of the HER-2 gene.

The invention will now be described in greater detail by reference to the following non-limiting examples.

EXAMPLE 1

Isolation and Biotinylation of Genomic Nucleic Acid

Isolation of Genomic Nucleic Acid

Genomic nucleic acid in this example was genomic DNA containing human HER-2 gene sequence from an individual with documented breast cancer or from a control individual without breast cancer. DNA was extracted either from serum of the individual or genomic DNA was isolated from paraffin-embedded tissue using EZ1 DNA kit from Qiagen.

Genomic DNA was obtained from the serum of 21 randomly selected individuals with breast cancer and 52 control individuals without breast cancer. Genomic DNA was also isolated from paraffin embedded tissue, genomic DNA were obtained from 92 randomly selected paraffin-embedded tissue samples with breast cancer and 26 control samples without breast cancer.

QIAamp MinElute Virus Spin Kit (Qiagen, Valencia, Calif.) was used for extracting DNA from paraffin-embedded tissue (FFPE). Breifly after deparaffinization by xylene/ethanol, FFPE tissue sections were treated with proteinase K, heat-inactivated (96° C., 10 min) and DNA was purified on silica membrane-packed spin column. Cell-free circulating DNA from plasma or serum (200 μl) was purified on the same kit according to the manufacturer's protocol. Genomic DNA was digested with DpnII for 1 hour at 37° C. The digestion was stopped by heat inactivation at 65° C. for 10 minutes.

Biotinylation of isolated DNA: DNA was biotinylated with biotin-16-dUTP using Biotin-Nick Translation Mix (Roche Applied Science, Basel, Switzerland) following the kit's instructions. The molar ratio of biotin-16-dUTP to dTTP in the mix is adjusted to ensure that every 20-25 nucleotide in the newly synthesized DNA is labeled with biotin, which gives the highest sensitivity for detection. The labeled fragments obtained in a typical nick translation reaction showed a size distribution of 200 to 500 base pairs.

The isolated and fragmented DNA from the above step was biotinylated using a standard nick translation (NT) protocol. A reaction mixture containing 10 μl of DNA was mixed with NT enzyme, buffer, and biotin-16-dUTP incubated at 65° C. for 1.5 hours. Reaction was terminated by adding 0.5 M EDTA and the mixture was incubated at 65° C. for 10 minutes. The genomic DNA (1 μg) was denatured in denaturation solution (70% deionized Formamide, 0.2×SSC) by incubation at 73° C. for 7 minutes then incubated on ice for 5 minutes.

Alternatively, isolated DNA was directly labeled with biotin by commercially available kits (e.g. Label IT® μArray® Biotin Labeling Kit).

EXAMPLE 2

Hybridization of Labeled Probes and Biotinylated Target DNA

FITC labeled probe complimentary to a region of the human HER-2 gene AND Cy-5 labeled chromosome 17 specific single copy sequence (17-SSC) was used for hybridizing to the biotinylated genomic DNA isolated from the serum or paraffin-embedded tissue sample.

The sequence of 17-SSC is provided below:

(SEQ ID NO: 1)
5' Cy5-TGTATTTATC CTCTCTCTAG CCATCCATAGC TGTAGCTGGC

TCACTCACT 3'

The probes were resuspended in Hybrisol VII hybridization solution (MP Biomedicals, Solon, Ohio), incubated at 37° C. for 30 minutes and denatured at 73° C. for 10 minutes. The probe mixture was then cooled on ice for 5 minutes. Denaturation solution (70% deionized Formamide, 0.2×SSC) was then added to the probe mixture.

The denatured probe mixture and denatured genomic DNA were then combined and incubated at 37° C. overnight.

EXAMPLE 3

Capture of Hybridization Complex on Solid Support and Detection by Flow Cytometry Hybridization complexes containing biotin-labeled genomic DNA were captured on streptavidin-coated beads.

Streptavidin-coated microspheres (Bangs Laboratories, Fishers, Ind.) were sequentially treated with BlockAid (Invitrogen, Carlsbad, Calif.) and sheared salmon sperm DNA (100 µg/mL) before conjugation to reduce non-specific binding. 5 µl of streptavidin beads (Bangs Lab, Fishers, Ind.) were washed once with 100 µl of conjugation buffer (100 mM Tris-HCL; pH 8.0, 0.1% Tween 20; and 1 M LiCl) and resuspended in 20 µl conjugation buffer. 5 µl probe-DNA complex was added to the beads and the mixture incubated while shaking at room temperature for one hour at room temperature to form a bead-DNA complex. The coupled beads are washed once with 10% formamide/0.2×SSC and twice with 0.2×SSC. The bead complex was resuspended in a solution containing rabbit anti-FITC antibody (BD Bioscience). The bead complex was washed three times with 2% BSA in phosphate buffered saline (PBS), resuspended in 4% blocking milk, and washed once with 2% BSA in PBS. The bead complex was resuspended in a solution containing Alexa-488 labeled goat anti-rabbit antibody (BD Bioscience) at a dilution of 1:500 and rotated for 30 minutes at room temperature in the dark. The bead complex was then washed once with 2% BSA in PBS using a Sorvall CW-2 Cell washer to wash and pellet the beads.

The fluorescent signal from FITC was further amplified by using the FITC/Alexa-488 dye combination. The fluorescent signals from FITC/Alexa-488 and Cy5 on the beads were detected as a change in fluorescence per bead as measured on a flow cytometer (Canto, BD San Jose, Calif.) following the manufacturer's instruction. The mean fluorescence intensity (MFI) of at least 5000 events was computed for each sample using the instrument's (Diva) software (BD, San Jose, Calif.)

EXAMPLE 4

Results of the Assay for Detecting Genetic Abnormalities in Genomic Nucleic Acid The ratio of signals from FITC/Alexa-488 and Cy-5 were measured. This ratio was representative of HER-2: 17-SSC ratio. Based on the results obtained from the control individuals or control samples, a ratio of 2.14 (mean ±3 SD) was considered as an amplification of HER-2 gene.

Results obtained using the method of example 4 were compared to results obtained from FISH, immunohistochemistry (IHC) and ELISA methods.

Using serum sample, there was a 90.5% and 90% concordance between the results of the present method and FISH and IHC respectively. The levels of HER-2 obtained from the serum samples using the present method were further compared to HER-2 levels obtained by ELISA method and using 12.3 ng/ml of serum as a cut-off. There was 52% concordance between the result of the two methods. This concordance level was similar to that reported for ELISA and IHC/cell-based testing methods 1) Kong S Y, et al: Serum HER-2 concentration in patients with primary breast cancer. J Clin Pathol 59:373-736, 2006; 2) Fornier M N et al: Serum HER-2 extracellular domain in metastatic breast cancer patients treated with weekly trastuzumab and paclitaxel: association with HER-2 status by immunohistochemistry and fluorescence in situ hybridization and with response rate. Ann Oncol 16:234-239, 2005.

Paraffin-embedded tissue samples from breast cancer patients were tested by the method of example 4, IHC and conventional FISH methods. Only the samples with either IHC 3+ or signal ratios of sample to control greater than 2.2 in conventional FISH are considered to be positive for HER-2 amplification, whereas cases with IHC 0/1+ staining or signal ratios of sample to control less than 1.8 in conventional FISH are interpreted as negative for HER-2 amplification. Samples with IHC 2+ are classified as inconclusive (or equivocal).

Among 122 cases examined, matched results from conventional FISH and the method of example 4 were obtained in 103 cases. In four cases with ratios greater than 2.2 in conventional FISH were found to be negative by the method of example 4, and 15 cases considered negative according to conventional FISH (ratios 1.8 or less) were tested positive by the method of example 4. Overall, concordance between conventional FISH and the method of example 4 was 84.4% (P<0.001).

Among 80 cases examined, matched results from IHC and the methods of example 4 were obtained in 63 cases. In eight cases which were considered positive for HER-2 over expression by IHC method were found to be negative by the method of example 4, and 9 cases considered to be negative by IHC method were found to be positive by the method of example 4. Overall, concordance between IHC and the method of example 4 was 78.8% (P<0.001).

Unless otherwise defined, all technical and scientific terms used herein have the same meaning as commonly understood by one of ordinary skill in the art to which this invention belongs. All nucleotide sequences provided herein are presented in the 5' to 3' direction.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other embodiments are set forth within the following claims.

What is claimed is:

1. A method for detecting a target sequence in genomic nucleic acid, comprising:
   a. contacting a sample of genomic nucleic acid comprising said target sequence with a probe specific for said target sequence to form a complex comprising said genomic nucleic acid and said probe hybridized to said target sequence, wherein said probe comprises a detectable label, and said target sequence has not been amplified;
   b. anchoring on a solid support said complex formed in step (a) through said genomic nucleic acid by means other than nucleic acid hybridization; and
   c. detecting the presence of said target sequence in said genomic nucleic acid by detecting association of said label with said solid support.

2. The method of claim 1, wherein said solid support comprises a first member of a binding pair and said genomic nucleic acid comprises a second member of the binding pair, and wherein binding of the binding pair members anchor said genomic nucleic acid to said solid support.

3. A method of claim 1, wherein said genomic nucleic acid is anchored covalently to said solid support.

4. The method of claim 1, wherein said solid support is a bead, a microwell plate, or a glass surface.

5. The method of claim 2, wherein said binding pair is a ligand-receptor, a hormone-receptor, or an antigen-antibody.

6. The method of claim 2, wherein said binding pair is biotin and streptavidin or variants of streptavidin.

7. The method of claim 1, wherein said probe is an oligonucleotide, an artificial chromosome, a fragmented artificial chromosome, a genomic DNA, an RNA, or a peptide nucleic acid.

8. A method of claim 1, wherein the length of the probe is at least 50 nucleotides.

9. The method of claim 1, wherein the detectable label is a fluorophore, nanoparticle, isotope, chemiluminiscent compound, enzyme, or hapten.

10. The method of claim 1, wherein said complex is detected on the solid support by flow cytometry.

11. The method of claim 1, wherein said complex is detected by detecting a labeled reagent that binds to the detectable label of the probe.

12. The method of claim 11, wherein said labeled reagent is a labeled antibody that is specific for the detectable label.

13. The method of claim 1, wherein said genomic nucleic acid is present in a test sample, and wherein said test sample is cells, tissues, body fluids, stool, paraffin embedded tissues, cell lysates, or tissue lysates.

14. A method for determining the presence or absence of a genetic abnormality in genomic nucleic acid, comprising:
   a. contacting a sample of genomic nucleic acid with a probe specific for said genetic abnormality to form a complex comprising said genomic nucleic acid hybridized to said probe if said genetic abnormality is present in said genomic nucleic acid, wherein said probe comprises a detectable label and said target sequence has not been amplified;
   b. anchoring on a solid support said complex formed in step (a) through said genomic nucleic acid by means other than nucleic acid hybridization; and
   c. determining the presence or absence of said genetic abnormality wherein detecting an association of said label with said solid support indicates the presence of said genetic abnormality, and wherein detecting no association of said label with said solid support indicates the absence of said genetic abnormality.

15. The method in claim 14, wherein said genetic abnormality is a chromosomal translocation, and first portion of said probe hybridizes to a region of a first chromosome of the translocation, and a second portion of said probe hybridizes to a region of a second chromosome of the translocation.

16. The method in claim 14, wherein the genetic abnormality is a duplication or deletion associated with a particular chromosomal segment or gene.

17. The method of claim 14, wherein said solid support comprises a first member of a binding pair and said genomic nucleic acid comprises a second member of the binding pair, and wherein binding of the binding pair members anchor said genomic nucleic acid to said solid support.

18. A method of claim 14, wherein said genomic nucleic acid is anchored covalently to the solid support.

19. The method of claim 14, wherein said genomic nucleic acid is genomic DNA.

20. The method of claim 14, wherein said solid support is a bead, a microwell plate, or a glass surface.

21. The method of claim 14, wherein said binding pair is a ligand-receptor, a hormone-receptor, or an antigen-antibody.

22. The method of claim 14, wherein said binding pair is biotin and streptavidin or variants of streptavidin.

23. The method of claim 14, wherein said probe is an oligonucleotide, an artificial chromosome, a fragmented artificial chromosome, a genomic DNA, an RNA, or a peptide nucleic acid.

24. A method of claim 14, wherein the length of the probe is at least 50 nucleotides.

25. The method of claim 14, wherein the probe is labeled with a fluorophore, nanoparticle, isotope, chemiluminiscent compound, enzyme, or hapten.

26. The method of claim 14, wherein said complex is detected on the solid support by flow cytometry.

27. The method of claim 14, wherein said complex is detected by detecting a labeled reagent that binds to the detectable label of the probe.

28. The method of claim 27, wherein said labeled reagent is a labeled antibody that is specific for the detectable label.

29. The method of claim 14, wherein said genomic nucleic acid is present in a test sample, and wherein said test sample is cells, tissues, body fluids, stool, paraffin embedded tissues, cell lysates, or tissue lysates.

30. A method for determining the presence or absence of a genetic abnormality in genomic nucleic acid, comprising:
   a. contacting a sample of genomic nucleic acid with a first probe specific for said genetic abnormality to form a first complex comprising said genomic nucleic acid hybridized to said first probe, if said genetic abnormality is present, wherein said probe comprises a detectable label, said genomic nucleic acid has not been amplified;
   b. anchoring on a solid support said complex formed in step (a) through said genomic nucleic acid by means other than nucleic acid hybridization;
   c. contacting a reference nucleic acid with a second probe specific for said reference nucleic acid to form a second complex comprising said reference nucleic acid hybridized to said second probe, wherein said second probe comprises a detectable label;
   d. anchoring on a solid support said complex formed in step (c) through said reference nucleic acid by means other than nucleic acid hybridization; and
   e. measuring the amount of said first complex formed by detecting the detectable label of said first probe associated with the complex and measuring the amount of second complex formed by detecting the detectable label of said second probe associated with the complex; and
   f. comparing the amount of said first complex to the amount of said second complex, wherein a difference in the amount of two complexes is an indicative of the absence of said genetic abnormality and a lack of a difference in the amount of two complexes is an indicative of the presence of said genetic abnormality.

31. The method of claim 30, wherein said reference nucleic acid is a house keeping gene or a single copy sequence in the chromosome.

32. The method of claim 30, wherein said genomic nucleic acid and said reference nucleic acid are obtained from the same sample.

33. The method of claim 32, wherein the detectable label of said first probe and said second probe are different.

34. The method of claim 30, wherein said genomic nucleic acid and said reference nucleic acid are obtained from different samples.

35. The method of claim 30, wherein the detectable label of said first probe and said second probe are different.

36. The method of claim 30, wherein said first probe and said second probe are same, and wherein said genomic nucleic acid and said reference nucleic acid are obtained from different samples.

37. A method for determining the presence or absence of a genetic abnormality in genomic nucleic acid, comprising:
   a. contacting a sample of genomic nucleic acid with a first probe specific for the genetic abnormality to form a first complex comprising said genomic nucleic acid hybridized to said first probe, if said genetic abnormality is present, wherein said probe comprises a detectable label and said genomic nucleic acid has not been amplified;
   b. anchoring on a solid support said first complex formed in step (a) through said genomic nucleic acid by means other than nucleic acid hybridization;
   c. contacting said sample of genomic nucleic acid with a second probe specific for a reference nucleic acid to form a second complex comprising said reference nucleic acid hybridized to the second probe, wherein said second probe comprises a detectable label;
   d. anchoring on a solid support said second complex formed in step (c) through said genomic nucleic acid by means other than nucleic acid hybridization;
   e. measuring the amount of said first complex formed by detecting the detectable label of said first probe associated with the complex and measuring the amount of second complex formed by detecting the detectable label of said second probe associated with the complex;
   f. obtaining a ratio of the amount of said first and said second complex; and
   g. comparing said ratio obtained to a ratio similarly obtained using genomic nucleic acid from a reference sample, wherein a difference in the ratio is indicative of the presence of said genetic abnormality and a lack of a difference in the amount of two complexes is an indicative of the absence of said genetic abnormality.

38. The method in claim 37, wherein the genetic abnormality is a duplication or deletion associated with a particular chromosomal segment or gene.

39. The method of claim 37, wherein said first complex and second complex are detected on said solid support by flow cytometry.

40. The method of claim 37, wherein the length of said first probe or said second probe is at least 50 nucleotides.

41. The method of claim 37, wherein said solid support consist of a first member of a binding pair and said genomic nucleic acid consist of a second member of the binding pair, and wherein binding of the binding pair members anchor said genomic nucleic acid to said solid support.

42. The method of claim 41, wherein said binding pair is biotin and streptavidin or variants of streptavidin.

43. The method of claim 37, wherein said genomic nucleic acid is genomic DNA.

44. The method of claim 37, wherein said reference nucleic acid is a house keeping gene or a single copy sequence in a chromosome.

45. A method of diagnosis of a disease in an individual, comprising,
   a. contacting a sample of genomic nucleic acid from the individual with a probe complementary to nucleic acid sequence specific for said disease to form a complex comprising said genomic nucleic acid and said probe if said genomic nucleic acid contains the nucleic acid sequence specific for said disease, wherein said probe comprises a detectable label and said target sequence of said genomic nucleic acid has not been amplified;
   b. anchoring on a solid support said complex formed in step (a) through said genomic nucleic acid by means other than nucleic acid hybridization;
   c. measuring the amount of said complex formed on said solid support by detecting the amount of detectable label associated with said support; and
   d. comparing the amount of complex formed to the amount of complex formed using genomic nucleic acid from a reference sample assayed under similar conditions, wherein a difference in amount of complex formed from the said individual as compared to the reference sample is diagnostic for said disease.

46. The method of claim 45, wherein said reference sample is taken from a normal individual.

47. The method of claim 45, wherein the method is used for measuring the tumor burden in an individual suspected of having cancer.

48. The method of claim 45, wherein said reference sample is obtained from the same individual after obtaining the test sample.

* * * * *

SEQUENCE LISTING

<160> NUMBER OF SEQ ID NOS: 1

<210> SEQ ID NO 1
<211> LENGTH: 50
<212> TYPE: DNA
<213> ORGANISM: Artificial Sequence
<220> FEATURE:
<223> OTHER INFORMATION: Description of Artificial Sequence: Synthetic probe

<400> SEQUENCE: 1
tgtatttatc ctctctctag ccatccatag ctgtagctgg ctcactcact         50